(12) United States Patent  
Escal (10) Patent No.: US 6,945,129 B2  
(45) Date of Patent: Sep. 20, 2005

(54) SAMPLE ANALYSIS APPARATUS (75) Inventor: Philippe Escal, Castelnau le Nez (FR)

(73) Assignee: Diagyr, Clapiers (FR)

( * ) Notice: Subject to any disclaimer, the term of this patent is extended or adjusted under 35 U.S.C. 154(b) by 0 days.

(21) Appl. No.: 10/311,537

(22) PCT Filed: Jun. 13, 2001

(86) PCT No.: PCT/FR01/01823  
§ 371 (c)(1),  
(2), (4) Date: Jul. 1, 2003

(87) PCT Pub. No.: WO01/96881  
PCT Pub. Date: Dec. 20, 2001

(65) Prior Publication Data  
US 2004/0020310 A1 Feb. 5, 2004

(30) Foreign Application Priority Data  
Jun. 16, 2000 (FR) ............................................ 00 07670

(51) Int. Cl.$^7$ ................................................ G01N 1/14
(52) U.S. Cl. ................. 73/864.24; 73/864.21; 73/863.01; 422/64; 422/72; 436/45; 494/10
(58) Field of Search ........................ 73/863.01–863.03, 73/864.21, 864.24; 422/72, 64, 100; 436/45; 494/10

(56) References Cited

U.S. PATENT DOCUMENTS

| | | | | |
|---|---|---|---|---|
| 3,953,172 A | * | 4/1976 | Shapiro et al. | 422/72 |
| 4,547,340 A | * | 10/1985 | Sanuki et al. | 422/64 |
| 4,683,120 A | * | 7/1987 | Meserol et al. | 422/72 |
| 4,708,940 A | * | 11/1987 | Yoshida et al. | 436/45 |
| 4,713,974 A | | 12/1987 | Stone | |
| 5,166,889 A | | 11/1992 | Cloyd | |
| 6,387,327 B1 | * | 5/2002 | Ricci et al. | 422/72 |
| 2003/0185710 A1 | * | 10/2003 | Matsuda et al. | 422/72 |

* cited by examiner

Primary Examiner—Hezron Williams  
Assistant Examiner—Nashmiya Fayyaz  
(74) Attorney, Agent, or Firm—Young & Thompson (57) ABSTRACT

An apparatus for analyzing liquid samples packed in tubes (6) closed with a top (7) capable of being perforated, includes a support (4) for the tubes and a unit (8) for sampling an aliquot from each tube and delivering it into a receptacle for treatment and/or analysis, the unit (8) including a hollow needle (45) connected to a suction/delivery device and vertically mobile; the support (4) has a circular tray provided with several tube-holders (5) on its periphery and capable of rotating about a vertical axis to bring a position successively and selectively the tubes (6) borne by the tube-holders (5) in line with the unit (8); each tube-holder (5) is connected to the tray (4) through a linkage (31) with two degrees of freedom.

14 Claims, 7 Drawing Sheets

SAMPLE ANALYSIS APPARATUS

BACKGROUND OF THE INVENTION

The present invention relates to an apparatus for the analysis of liquid samples in sample tubes closed by a pierceable stopper.

Such apparatus is used at present particularly in the fields of chemistry, biochemistry and biology to analyze various liquids by different analysis techniques, as for example liquid chromatography. For example, this apparatus is used by medical analysis laboratories to analyze blood and other liquids of human or animal origin.

DESCRIPTION OF THE RELATED ART

International patent application WO90/03834 discloses an automatic apparatus for the treatment and analysis of blood serum comprising a first support in the form of a rack adapted to receive test tubes closed by a pierceable stopper and containing samples of blood and a separator gel, a centrifugation unit capable of receiving several test tubes to subject their contents to centrifugation, an optical detection unit adapted to receive individually the test tubes which have been subjected to centrifugation, and to generate output signals indicating whether the centrifugation has been correctly carried out and indicating the position of the separator gel layer between the serum and the red blood cells, and a computer which analyzes the output signals from the optical detection unit. The apparatus described in this document moreover comprises a unit for removing and distributing, comprising a hollow needle which can be moved vertically downwardly to perforate the stopper of a test tube placed in an optical detection unit, so as to remove a serum sample in this test tube. The apparatus moreover comprises a second support in the form of a rack, which supports empty bowls adapted to receive samples of serum removed from the test tubes individually brought to the optical detection unit, a third support in the form of a rack, adapted to receive the centrifuged test tubes which the optical detection unit has detected as being defective, a fourth support in the form of a rack, adapted to receive the test tubes and the bowls containing the serum samples removed respectively from the test tubes, each bowl surmounting the associated test tube, and a robot arm adapted to take the samples one by one from the first support, to transfer them into the centrifugation unit and from there, one by one, into the optical detection unit. If this latter reveals an unsatisfactory result of centrifugation, the robot arm removes the defective test tube and will place it in the third rack, them it will get a new sample from the centrifugation unit to place it in the optical detection unit. On the contrary, if the optical detection unit reveals that the test tube which is located therein has undergone a correct centrifugation, the needle of the removal and distribution unit is lowered to perforate the stopper of the test tube and its lower end is immersed in the serum to a level located above the layer of separator gel, as a function of the position of this layer detected by the optical detection unit. The removal and distribution unit then removes a sample of serum from the test tube, then the hollow needle is withdrawn from this latter. The robot will then get from the second support an empty bowl and bring it below the hollow needle. The removal and distribution unit will then deliver the sample of the serum removed from the empty bowl, then the robot places the filled bowl and the serum sample on the stopper of the test tube which is located at this moment in the optical detection unit. Finally, the test tube and the associated bowl are transferred by the robot from the optical detection unit to the fourth support. The operations described above are repeated successively for each of the test tubes contained in the centrifugation unit.

The known apparatus briefly described above is relatively complicated and voluminous, and its capacity per unit time of treatment is relatively limited, given the large number of transfer operations the robot must carry out to transfer each test tube and/or the associated bowl between the different units and the different supports in the form of racks provided in the apparatus.

U.S. Pat. No. 4,713,974 discloses an analyzer robot comprising a carousel which can turn about a vertical axis and on which several racks are fixed removably. Each rack comprises three series of cylindrical cells, with vertical axes, adapted to receive containers of the samples to be analyzed and each closed by a pierceable stopper. When the racks, provided with containers, are fixed on the plate of the carousel, the containers are disposed in three concentric circles centered on the axis of rotation of the plate of the carousel, and the containers are aligned radially in groups of three containers. Thus, by turning the carousel stepwise, it is possible to bring each time a group of three containers to a fixed working station located near the periphery of the plate of the carousel. In this workstation is located a unit for removal and distribution comprising a hollow needle extending vertically, which is connected to a suction/delivery means and which is mounted on a spring such that its lower end is located at a level slightly higher than that of the stoppers of the containers. In addition to its movement of rotation, the carousel plate can be given a horizontal translatory movement in a radial direction relative to the axis of rotation of the plate, toward and spaced from the workstation, such that any container selected from among three radially aligned containers and present at a given time at the workstation can be brought below the needle of the removal and distribution unit, into vertical alignment with said needle. The plate of the carousel comprises several holes which are aligned respectively with the holes formed in the bottom of the cells of the racks fixed on the plate. The removal and distribution unit moreover comprises an elevator, in the form of a vertical rod, which is aligned axially with the needle and which can be moved vertically upwardly through a hole in the plate of the carousel to raise the selected container which has been brought into vertical alignment with the needle. Because of the raising of the selected container, the stopper of this latter impales itself on the needle and the raising of the container is continued until the lower end of the needle abuts against the bottom of the container.

The analysis robot described in U.S. Pat. No. 4,713,974 is substantially more compact than the apparatus described in the international patent application WO90/03834, and it permits avoiding numerous transfers and manipulations which must be carried out for each test tube in the apparatus described in the mentioned international patent application. However, the analysis robot of U.S. Pat. No. 4,713,974 does not permit subjecting the content of the containers to centrifugation. In the case in which the liquid samples must be centrifuged before being analyzed, centrifugation must therefore be carried out in a conventional centrifuge.

U.S. Pat. No. 4,478,095 discloses an analysis robot similar to that which is described in U.S. Pat. No. 4,713,974. It differs essentially by the fact that the carousel comprises a principal plate which can be given only a rotatable movement and which carries four planetary auxiliary plates that can be turned relative to the principal plate, each auxiliary plate comprising several cells disposed in a single circle and its periphery to receive containers of liquid samples to be analyzed. A drive device comprising an electric motor and a transmission system with belts and pulleys, as well as an electromagnetic brake and an electromagnetic clutch permit selectively turning either the principal plate with the auxiliary plates without the latter being able to turn relative to the principal plate, or the auxiliary plates without the principal plate being able to turn, according to whether the electromagnetic brake or the electromagnetic clutch is excited. Thus, by turning first of all the principal plate, then the auxiliary plates, it is possible to bring any selected container to the workstation where the removal and distribution unit is located. Here again, the carousel of the analysis robot of U.S. Pat. No. 4,478,095 does not permit centrifuging the liquid samples contained in the containers carried by the auxiliary plates of the carousel, such that if the liquid products to be analyzed must be centrifuged before analysis, the centrifugation must be carried out in a conventional centrifuge before placing the containers in the cells of the planetary auxiliary plates of the carousel of the analysis robot.

SUMMARY OF THE INVENTION

The present invention thus has for its object to provide an analysis robot which permits, as needed, centrifuging the liquid samples to be analyzed, whilst being more compact and capable of processing per hour a larger number of liquid samples than the apparatus described in international patent application WO90/03834.

To this end, the invention has for its object an apparatus for the analysis of liquid samples in test tubes closed by a pierceable stopper, comprising a support adapted to support in vertical position the sample tubes, a removal and distribution unit to remove from each sample tube carried by the support a portion of the liquid sample contained in the sample tube and to distribute at least a fraction of the removed portion of liquid sample into at least one receptacle for processing and analysis of said distributed fraction, said removal and distribution unit comprising a hollow needle which is connected to a suction/distribution means and fixed in vertical position to a vertically movable needle carrier, and drive means to move vertically the needle carrier between a first position in which the lower end of the needle is located at a level higher than that of the cork of said sample tube carried by the support, and a second position in which the lower end of the needle is within the liquid contained in said sample tube carried by the support, characterized in that said support is constituted by a circular plate provided with several tube carriers which are disposed at intervals about its periphery and which each comprise a recess with a vertical axis to receive and support a sample tube, said circular plate being adapted to turn about a vertical axis to bring and position successively and selectively the tube carriers to a workstation where the removal and distribution unit is located, such that this latter can act on the sample tube supported by the tube carrier brought to and positioned in the workstation, in that each tube carrier is connected to the circular plate by a connection with two degrees of freedom, namely freedom of vertical movement of translation and freedom of movement of rotation about a horizontal axis oriented tangentially relative to the circular plate, and in that at the workstation is disposed a bearing means adapted to support from below the tube carrier brought to and positioned in the workstation.

Thus, with the apparatus according to the invention, if the liquid samples must be centrifuged so as to separate them into at least two phases for analysis of at least one of the two phases of each sample, it suffices to turn the rotatable plate at a suitable speed of rotation for centrifugation. Thanks to the fact that each tube carrier is connected to the turning plate by a connection with two degrees of freedom permitting rotational movement of each tube carrier about a horizontal axis tangential to the turning plate, each sample tube can, under the action of centrifugal force, take a horizontal or substantially horizontal position which is particularly favorable to the separation of the phases of the sample liquids by said centrifugal force. When the speed of rotation of the plate is then reduced so as selectively and step by step to bring the tube carrier to the workstation, the sample tubes automatically return, by gravity, to a vertical position.

Each time the turning plate is stopped to immobilize a sample tube in the workstation, the needle of the removal and distribution unit can be lowered to pierce the stopper of the sample tube immobilized in the workstation and to remove from this tube a sample of desired quantity (aliquot) of the liquid sample or of the desired phase of this liquid sample. Thanks to the fact that each tube carrier has freedom of movement vertically in translation and thanks to the support means which permit supporting from below the tube carrier brought to and positioned in the workstation, the vertical forces, which are applied to the stopper of the sample tube at the moment it is pierced by the needle of the removal and distribution unit and which can sometimes amount to several dozens of Newtons, is not transmitted by the tube carrier to the turning circular plate. As a result, this latter is not in danger of being deflected by the vertical forces mentioned above. Stated otherwise, if the plate were deflected, vibration forces would be produced each time the plate is driven at high speed, during the centrifugation steps. These vibrations would lead to rapid wear of the roller bearings of the plate and would have an undesirable influence on the separation of the liquid samples into several phases.

Because the circular turning plate is freed from the above-mentioned vertical forces, it does not need to have high rigidity and it can be relatively light, and hence have a low inertia. This permits using an electric motor of low power and consuming less electrical energy for driving the plate in rotation. Moreover, thanks to its light weight, the turning plate can be stopped more easily and with greater precision for the positioning of the sample tubes below the needle of the removal and distribution unit.

The apparatus according to the invention can moreover have one or several of the following characteristics:

each tube carrier is constituted by a cylindrical sleeve which is open at its upper end and closed at its lower end, and which comprises, adjacent its upper end, two aligned pivots which define the horizontal axis of the connection with two degrees of freedom;

the upper end of each cylindrical sleeve is disposed between two legs of a mounting member in the form of a fork, which is secured to the circular plate and whose two legs extend radially outwardly of said circular plate, the two pivots of the cylindrical sleeve being supported respectively by the legs of the mounting piece by means of the connection with two degrees of freedom;

each leg of the mounting piece comprises a vertical notch, in which is engaged one of the two pivots of the cylindrical sleeve;

in a first embodiment of the invention, each of the two pivots is supported resiliently in the corresponding vertical notch by a flexible spring;

each vertical notch is formed in the upper surface of the corresponding leg of the mounting member and the flexible spring is disposed in the vertical notch between the bottom of the latter and the pivot;

in this case, the mounting member carries removable retaining means which, in service, retain the two pivots in the corresponding vertical notches;

in a modified embodiment, each vertical notch is formed in the lower surface of the corresponding leg of the mounting member and the flexible spring is constituted by a flexible blade, of which one end is fixed to the lower surface of said corresponding leg and of which the other end resiliently supports and retains the pivot in the corresponding vertical notch;

in one or the other case, the support means can be constituted by fixed stop disposed below the lower end of the cylindrical tube-carrying sleeve brought to and positioned in the workstation, at a vertical distance from said lower end which is smaller than a maximum path of vertical movement which is permitted the cylindrical tube-carrying sleeve by said connection with two degrees of freedom and by the flexible spring when the needle of the removal and distribution unit exerts a vertical penetration force, directed downwardly, against the stopper of the sample tube in said cylindrical tube-carrying sleeve;

in another embodiment, each vertical notch is formed in the upper surface of the corresponding leg of the mounting member and each pivot rests on the bottom of the corresponding vertical notch;

in this case, the support means can be constituted by a wedge, which can be moved by an actuator between a first position in which said wedge does not interfere with the cylindrical tube-carrying sleeves when the circular plate is rotated, and a second position in which said wedge is in contact with the end of the cylindrical tube-carrying sleeve brought to and positioned in the workstation and supports said cylindrical sleeve in a vertical position such that its two pivots no longer rest on the bottom of the corresponding vertical notches in the legs of the mounting member;

said wedge is constituted by a piece in the form of a wedge which can slide, under the control of the actuator, over a fixed horizontal support and guide surface;

each mounting member comprises an abutment means adapted to prevent the cylindrical tube-carrying sleeve from pivoting about the horizontal axis defined by the two pivots and to hold said cylindrical sleeve in a vertical position when the wedge is moved from its first to its second position by the actuator and comes in the course of movement into contact with the lower end of said cylindrical sleeve;

in all embodiments, the circular plate is preferably connected to drive means adapted to turn said circular plate selectively at a first relatively rapid speed to subject to centrifugation the liquid samples contained the sample tubes carried by the circular plate, and at a second speed, substantially slower than the first speed, to bring and position successively and selectively said sample tubes to the workstation;

in all embodiments, the tube-carrying cylindrical sleeves can be made of a transparent material or each sleeve can comprise a wide window in its cylindrical wall, so as to permit reading an individual identification code carried by a label fixed to each sample tube, by a code reader installed at a fixed station in a predefined angular position relative to the vertical axis of rotation of the circular plate.

BRIEF DESCRIPTION OF THE DRAWINGS

Other characteristics and advantages of the invention will become apparent from the following description given by way of example with reference to the accompanying drawings, in which.

DESCRIPTION OF THE PREFERRED EMBODIMENTS

The analysis robot shown in FIGS. 1 to 3 comprises a housing 1, whose upper plate 2 has a large circular opening 3, which exposes a rotatable circular plate 4 located below the opening 3. Several tube carriers 5, adapted each to support a sample tube 6 closed by a stopper 7, are mounted at the periphery of the plate 4 in a manner that will be described in greater detail later.

The upper plate 2 of the housing 1 supports at least one and preferably two removal and distribution units 8 and 9 which will described in detail later.

The plate 4 is disposed in a bowl 11 (FIG. 3), for example a bowl with a circular edge, whose diameter is substantially greater than that of the plate 4. At the middle of the bowl 11 is located a cylindrical well 12 which projects upwardly from the bottom 11a of the bowl 11. The circular plate 4 is fixed at the upper end of a vertical hollow shaft 13 which extends downwardly within the well 12 and is mounted rotatably in the latter by means of roller bearings 14 and 15. The plate 4 and the shaft 13 can be made in a single piece, preferably of a light material, for example a plastic material or a light metal such as aluminum or aluminum alloy. The bowl 11 is supported by a horizontal plate 16, which forms a part of the housing 1, by means of several small column crosspieces 17, so as to provide a space 18 between the plate 16 and the bottom 11a of the bowl 11. The lower end of the hollow shaft 13 projects into the space 18. The hollow shaft 13 and thus the plate 4 can be driven in rotation by an electric motor 19, preferably a stepping motor, which is fixed to the plate 16 below the latter, the output shaft of the motor 19 passes through the plate 16 and carries, at its upper end, in the space 18, a toothed pulley 21, which is connected kinematically by a toothed belt 22 to another toothed pulley 23 which is fixed at the lower end of the hollow shaft 13.

Figure 4A:
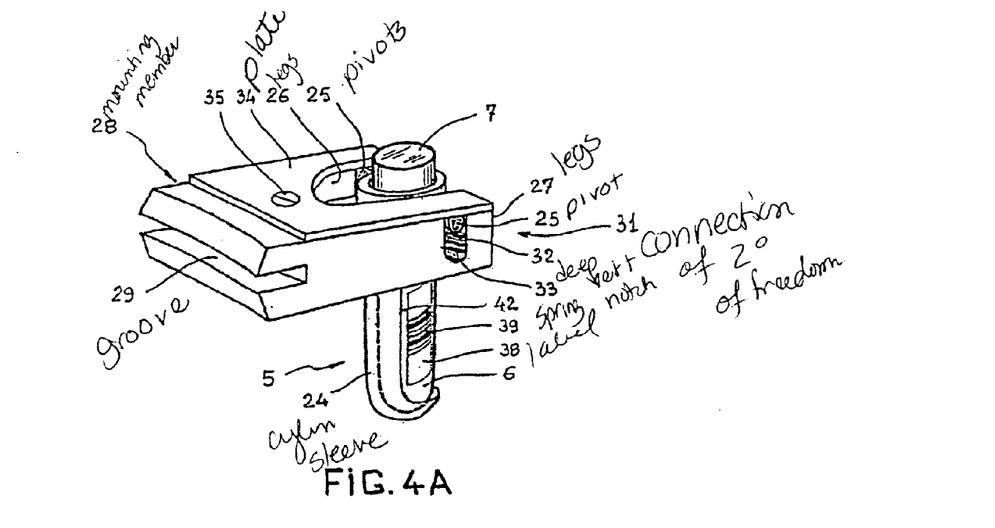
FIG. 4A is a perspective view, on a larger scale, showing one of the tube carriers used in the analysis robot of FIGS. 1 to 3.

As shown in FIG. 4A, each tube carrier is preferably constituted by a cylindrical sleeve 24, which is open at its upper end and closed at its lower end. Each sleeve 24 comprises, adjacent its upper end, two pivots 25 whose axes are aligned and perpendicular to the longitudinal axis of the tube 24. The upper end of each sleeve 24 is disposed between the two legs 26 and 27 of a mounting member 28 in the form of a fork, which is fixed to the circular plate 4, at the periphery of this latter. For example, the mounting member 28 comprises, on the side opposite the two legs 26 and 27, a groove 29 whose width corresponds to the thickness of the edge of the circular plate 4. The mounting member 28 is fitted around, by its groove 29, the edge of the circular plate 4 and it is fixed to the latter by gluing, by welding, by screws or by any other suitable securement means. Once the mounting member 28 is fixed to the plate 4, the legs 26 and 27 extend radially outwardly of the plate.

The two pivots 25 of the sleeve 24 are supported by the legs 26 and 27 of the mounting member 8 by means of a connection 31 with two degrees of freedom, which gives to the sleeve 24 the possibility of having a vertical translatory movement and a movement of rotation about a horizontal axis which is oriented tangentially to the circular plate 4 and which is defined by the two pivots 25. More precisely, as shown in FIG. 4A, each of the two legs 26 and 27 of the mounting member 28 comprises, in its upper surface, a deep vertical notch 32 in which is engaged one of the two pivots 25 of the sleeve 24. A flexible spring 33, for example a helicoidal spring, is disposed in each of the two notches 32, between the bottom of the latter and the pivot 25. A plate 34, cut out in the form of a U, is fixed detachably by at least one screw 35 to the upper surface of the mounting member 28 such that, in service, the plate 34 covers the notches 32 thereby to retain the pivots 25.

Figure 4B:
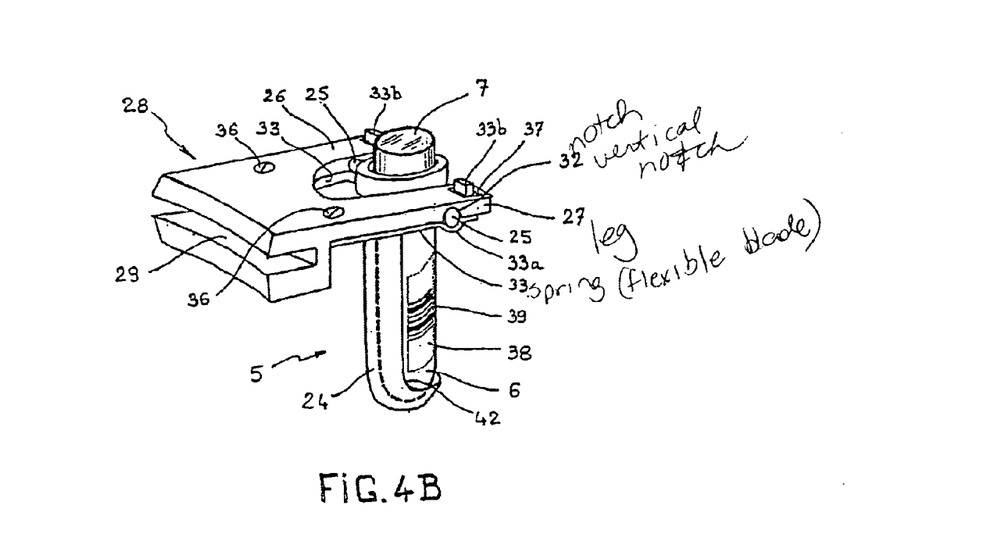
FIG. 4B shows a modified embodiment of the tube carrier of FIG. 4A.

FIG. 4B shows a modified embodiment of the connection 31 with two degrees of freedom. In FIG. 4B, the elements which are identical or which play the same role as those in FIG. 4A are designated by the same reference numerals. In the modified embodiment of FIG. 4B, each vertical notch 32 is formed in the lower surface of the corresponding leg 26 or 27 of the mounting member 28 and each flexible spring 33 is constituted by a flexible blade, of which one end is fixed to the lower surface of the leg 26 or 27 by a nut and bolt assembly or by a screw 36. The other end of each spring blade 33 resiliently supports and retains the pivot 25 in the corresponding vertical notch 32. This latter can have for example a semicircular profile, of which the diameter corresponds to the external diameter of the pivot 25. In this case, each spring blade 33 comprises rounded portion 33a, which also has a semicircular profile matching the external cylindrical surface of the pivot 25. Preferably, each spring blade 33 moreover comprises, at its free end, a portion 33b which is elbowed at a right angle upwardly and engaged in an opening 37 formed in the corresponding leg 26 or 27 of the mounting member 28. The two elbowed portions 33b permit preventing the pivots 25 from radially outwardly escaping beyond the free ends of the spring blades 33 when these latter are bent downwardly under the action of a vertical force applied to the stopper 7 of the sample tube 6 supported by the sleeve 24.

Figure 5:
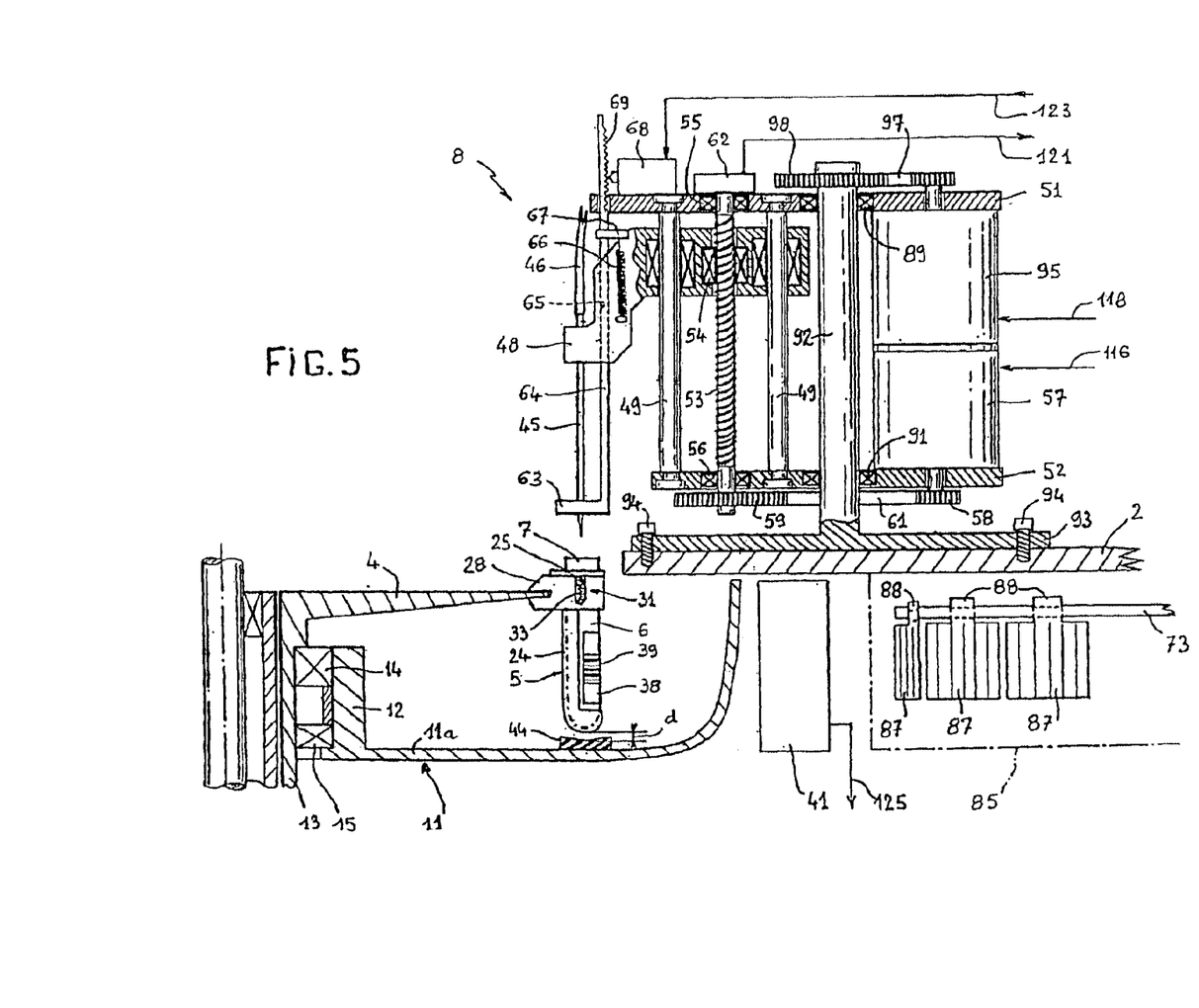
FIG. 5 is a view partially in elevation and partially in cross-section on the line V—V of FIG. 1, the needle of the removal and distribution unit being shown in the upper position.
Figure 6:
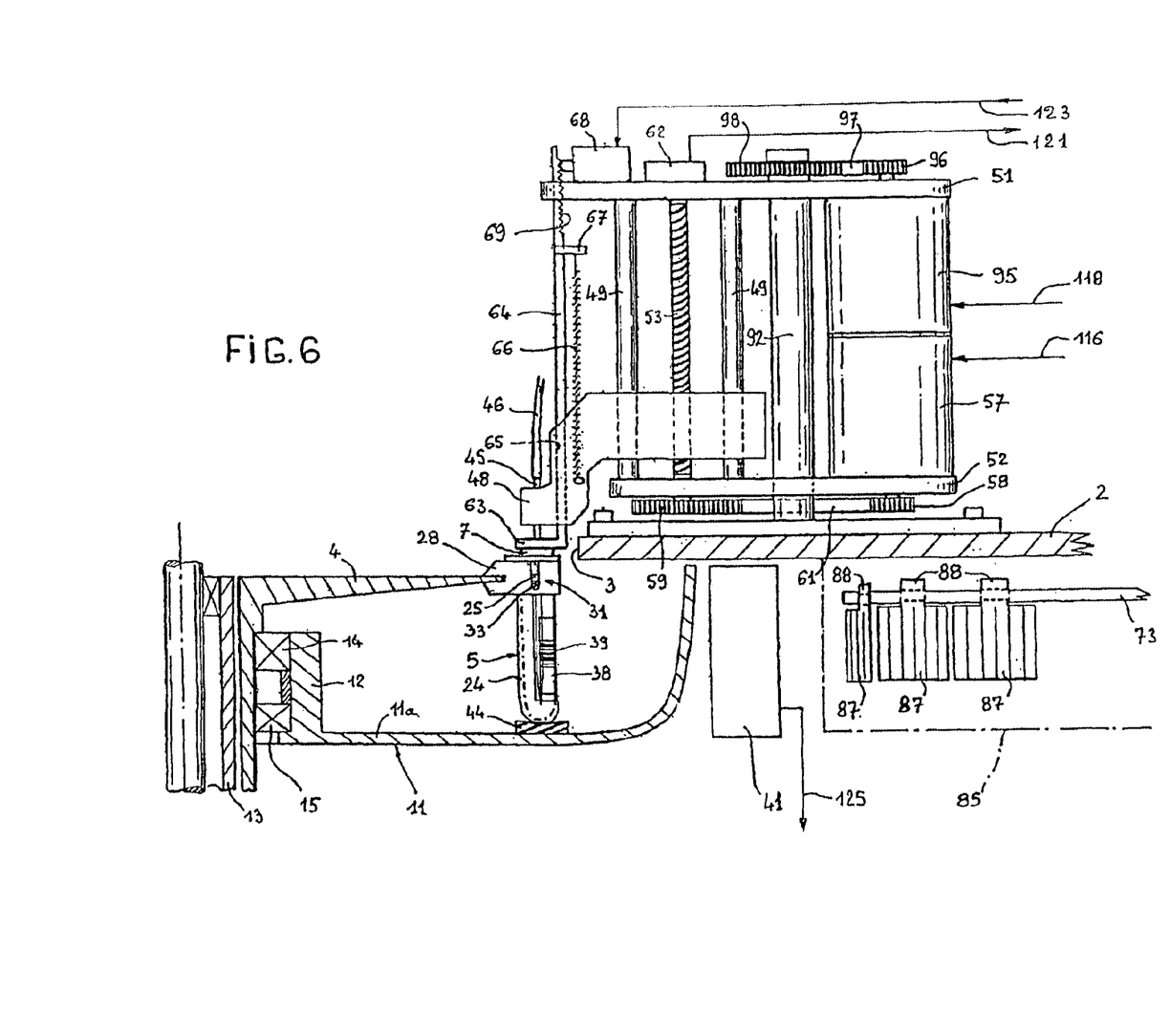
FIG. 6 is a view similar to FIG. 5, the needle of the removal and distribution unit being shown in a lower position.

Each sample tube 6 is provided, in a known manner, with a self-sticking label 38 carrying an identification code 39, for example in the form of a barcode, which can be read by a code reader 41 installed at a fixed station in a predefined angular relation to the vertical axis of rotation of the circular plate 4. For example, as shown in FIGS. 5 and 6, the code reader 41 can be disposed outside the bowl 11, below an upper plate 2 of the casing 1, in line with the removal and distribution unit 8. To permit reading of the identification code 39 carried by the label 38 of each sample tube 6, each tube-carrying sleeve 24 comprises, in its cylindrical wall, a wide window 42. By way of modification, each sleeve 24 could be made of a transparent material, for example a transparent plastic material. Similarly, the bowl 11 is made of transparent plastic material or a portion of its peripheral wall located facing the code reader 41 comprises a window.

Thus, each time a sample tube 6 is brought in position by the turning circular plate 4 into an angular position corresponding to the position of the removal and distribution unit 8, the code 39 carried by the label 38 of the sample tube 6 can be read by the code reader 41. It should be noted that the code reader 41 is not necessarily located in a position corresponding to that of the removal and distribution unit 8. In fact, the code reader 41 could be installed in anywhere along the periphery of the bowl 11. Thus, an angular coder 43 (FIG. 3), associated for example with the electric motor 19 (it could as a modification be associated with the turning circular plate 4), permits knowing at any time the angular position of the plate 4. As a result, if the code reader 41 is installed in a different angular position from that of the removal and distribution unit 8, to bring any one of the sample tubes 6 of which the identification code 39 has been read by the code reader 41, it suffices to turn the circular plate 4 through an angle corresponding to the angular spacing between the angular positions in which are located respectively the code reader 41 and the removal and distribution unit 8 at the periphery of the bowl 11.

Figure 3:
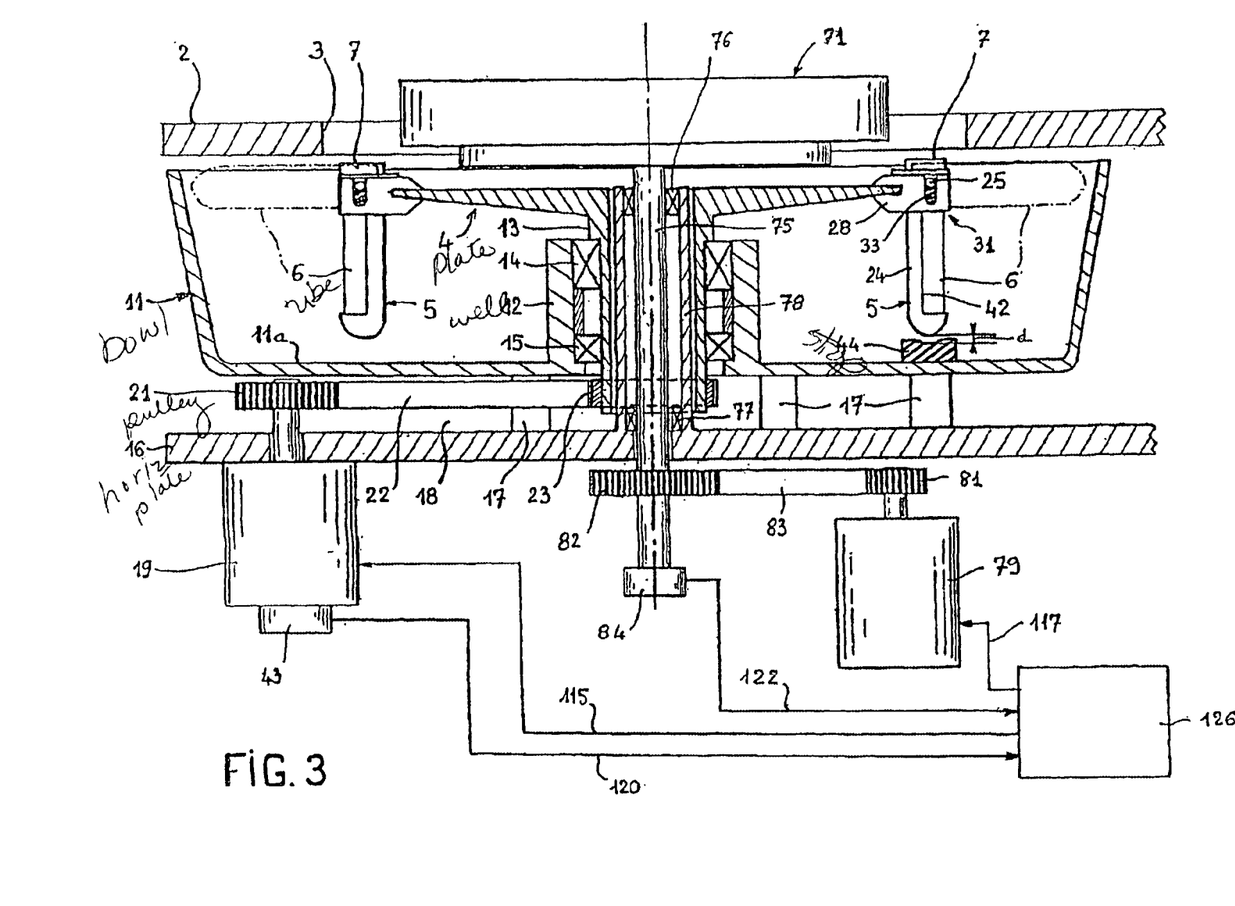
FIG. 3 is a view partially in elevation and partially in cross-section on the broken line III—III of FIG. 1.

Referring now to FIGS. 3, 5 and 6, there can be seen a stop 44, for example of hard rubber, which is fixed on the bottom 11a of the bowl 11 at a position such that the stop 44 will be vertically aligned with the tube-carrying sleeve 24 which, at a given time, is positioned in correspondence with the removal and distribution unit 8. The upper surface of the stop 44 is located at a vertical distance d from the lower end of the tube-carrying sleeve 24, which is smaller than the maximum path of vertical movement which is permitted the sleeve 24 by the above-mentioned connection 31 with two degrees of freedom, in combination with the spring 33. As will be seen later, the stop 44 serves as a bearing means for the sleeve 24 when the removal and distribution unit 8 removes a liquid sample (aliquot) from the sample tube 6 supported by said sleeve.

Figure 2:
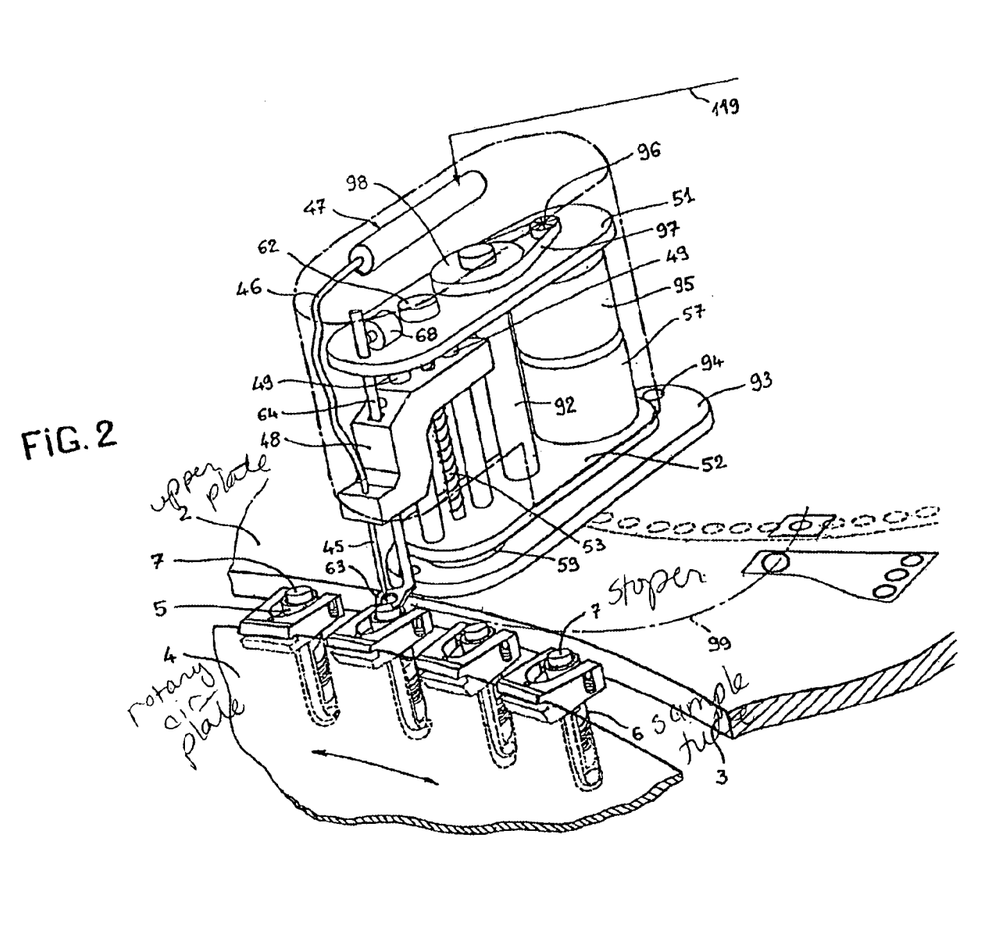
FIG. 2 is a partial perspective view showing a removal and distribution unit of the analysis robot of FIG. 1.

The removal and distribution unit 8 comprises, in a manner known per se, a hollow needle 45, which is connected by a flexible tube 46 to a suction/delivery means 47 which can for example be constituted by a syringe whose piston can be moved by an actuator, and which is shown only schematically in FIG. 2 as such a syringe and the manner in which it is connected to the hollow needle 45 are well known, for example from the two U.S. Pat. Nos. 4,478,095 and 4,713,974 mentioned above.

Differently from the analysis robots described in these two American patents, the hollow needle 45 of the removal and distribution unit 8 of the analysis robot according to the invention is fixed in vertical position to a needle carrier 48 which can be moved vertically between one position (FIG. 5) in which the lower end of the needle 45 is located at a level higher than that of the stopper 7 of the sample tube 6 which has been brought at a given time into correspondence with the removal and distribution unit 8, and a second position (FIG. 6) in which the lower end of the needle, after having pierced the stopper 7, is located within the liquid contained in said sample tube.

To this end, the needle carrier 48 is slidably mounted on two guide columns 49 whose upper and lower ends are fixed rigidly respectively to an upper horizontal plate 51 and to a lower horizontal plate 52. An endless screw 53 is disposed vertically between the two columns 49 and is in engagement with a nut 54, for example a ball nut, fixed to the needle carrier 48. The screw 51 is mounted rotatably in bearings 55 and 56, for example roller bearings, carried respectively by the plates 51 and 52. The screw 53 can be driven in rotation by an electric motor 57, for example a stepping motor, which is fixed to the plate 52, and by a transmission constituted for example by two toothed pulleys 58 and 59 which are fixed respectively to the output shaft of the motor 57 and to the lower end of the screw 53, and by a toothed belt 61.

An angular coder 62 carried by the plate 51 and associated with the screw 53 permits at any time knowing the number of turns or fractions of turns made by the screw 53, and hence the position height-wise of the needle carrier 48 and the needle 45. Thus, by giving the stepping motor 57 a suitable number of impulses, it is possible to bring the needle carrier 48 into any desired vertical position under the control of the angular coder 62. In particular, the lower end of the needle 45 can be brought to the desired depth within the liquid sample contained in the sample tube 6 which at a given time has been brought to and positioned in correspondence with the removal and distribution unit 8.

When the needle carrier 48 is lowered to remove an aliquot from the sample tube 6, the needle 45 first perforates the stopper 7 of the tube 6. This done, the needle 45 applies to the stopper 7 a force whose intensity can vary according to the nature and/or the thickness of the stopper 7. If this force, which can reach several tens of Newtons, were applied to the circular plate 4, it could be prejudicial to the good operation of this plate. It is thus important that this force not be transmitted to the plate 4. This problem is solved in combination with the above-mentioned connection 31 with two degrees of freedom, which connects each tube carrier 5 (sleeve 24) to a corresponding mounting member 28 fixed to the plate 4, and by the support means constituted by the stop 44. Thus, under the action of the force exerted by the needle 45 on the cork 7, the pivots 25 of the sleeve 24 are displaced downwardly, against the opposite force of the flexible springs 33, in the vertical notches 32 of the mounting member 28, until the lower end of the sleeve 24 comes into contact with the upper surface of the stop 44, which thus absorbs entirely the vertical force exerted by the needle 45 on the stopper 7. It is to be noted that the springs 33 must have a high flexibility so as to transmit only a very small vertical force to the mounting member 28, hence to the circular plate 4.

With the needle carrier 48 can be associated a pusher 63 in the form of a foot which surrounds the lower end of the needle 45 and which is fixed to the lower end of a rod 64 mounted slidably in a vertical hole 65 in the needle carrier 48 (FIGS. 2, 5 and 6). A helicoidal spring 66 is attached by its lower end to the needle carrier 48 and by its upper end to a securement tongue 67 which is itself fixed to the rod 64 above the needle carrier 48. The rod 64 can be blocked by blocking means 68 fixed to the plate 51. The blocking means 68 can for example be constituted by an electromagnet whose core has an end formed like a wedge that can be engaged between the teeth of a rack 69 formed on the upper portion of the rod 64.

When the core of the electromagnet 68 is spaced from the rack 69, and the needle carrier 48 is lowered by means of the screw 53, the rod 64 and the foot 63 are also lowered until the foot comes into contact with the stopper 7, whilst the lower end of the sleeve 24 is in contact with the stop 44. At this time, the descending movement of the rod 64 stops and the spring 66 is stressed while the needle carrier 48 continues its descent until the lower end of the needle 45 reaches the desired depth within the sample tube 6. Under the influence of the tension of spring 66, the foot 63 holds the sleeve 24 in contact with the stop 44. While the needle 45 removes a liquid sample from the tube 6, the electromagnet 68 can be actuated such that its core engages between two teeth of the rack 69 to block the rod 64. After the desired quantity of liquid sample (aliquot) has been removed from the sample tube 6, the needle carrier 48 is raised to its upper position by means of the endless screw 53, the raising being helped by the spring 66 which is tensioned. During the rising of the needle carrier 48, the electromagnet 68 continues to block momentarily the rod 64 so as to hold the foot 63 in engagement against the stopper 7 of the sample tube 6 and thereby to prevent the stopper 7 and the tube 6 from being raised by friction exerted between the needle 45 and the stopper 7. After the needle carrier 48 has been raised an amount such that the needle 45 has been completely withdrawn from the tube 6 and the stopper 7, the electromagnet 68 is actuated so as to free the rod 64. Then, when the needle carrier 48 continues its rising movement, it encounters the securement tongue 67, thereby causing the raising of the rod 64 and the foot 63.

In the case in which liquid samples (aliquots) removed from the sample tubes 6 are subjected to chromatographic analysis, the liquid sample removed at a given moment can be brought into an analysis loop (not shown) interposed in known manner between the needle 45 and the syringe 47. Chromatographic analysis can also be carried out after distribution of the liquid sample into one of the receptacles 74 of the plate 73 described later.

In the case in which the liquid samples removed from the sample tubes 6 must be treated by one or several reagents, the analysis robot according to the invention can moreover comprise a reagent carrying plate 71 (FIG. 1) of circular shape, at the periphery of which are fixed several cups or containers 72 each containing a reagent, as well as another plate 73 (FIGS. 1 and 5) also of circular shape, at the periphery of which are disposed several receptacles 74 adapted to receive liquid samples removed from the sample tubes 6 by the removal and distribution unit 8 and one or several reagents removed by the removal and distribution unit 9.

Figure 1:
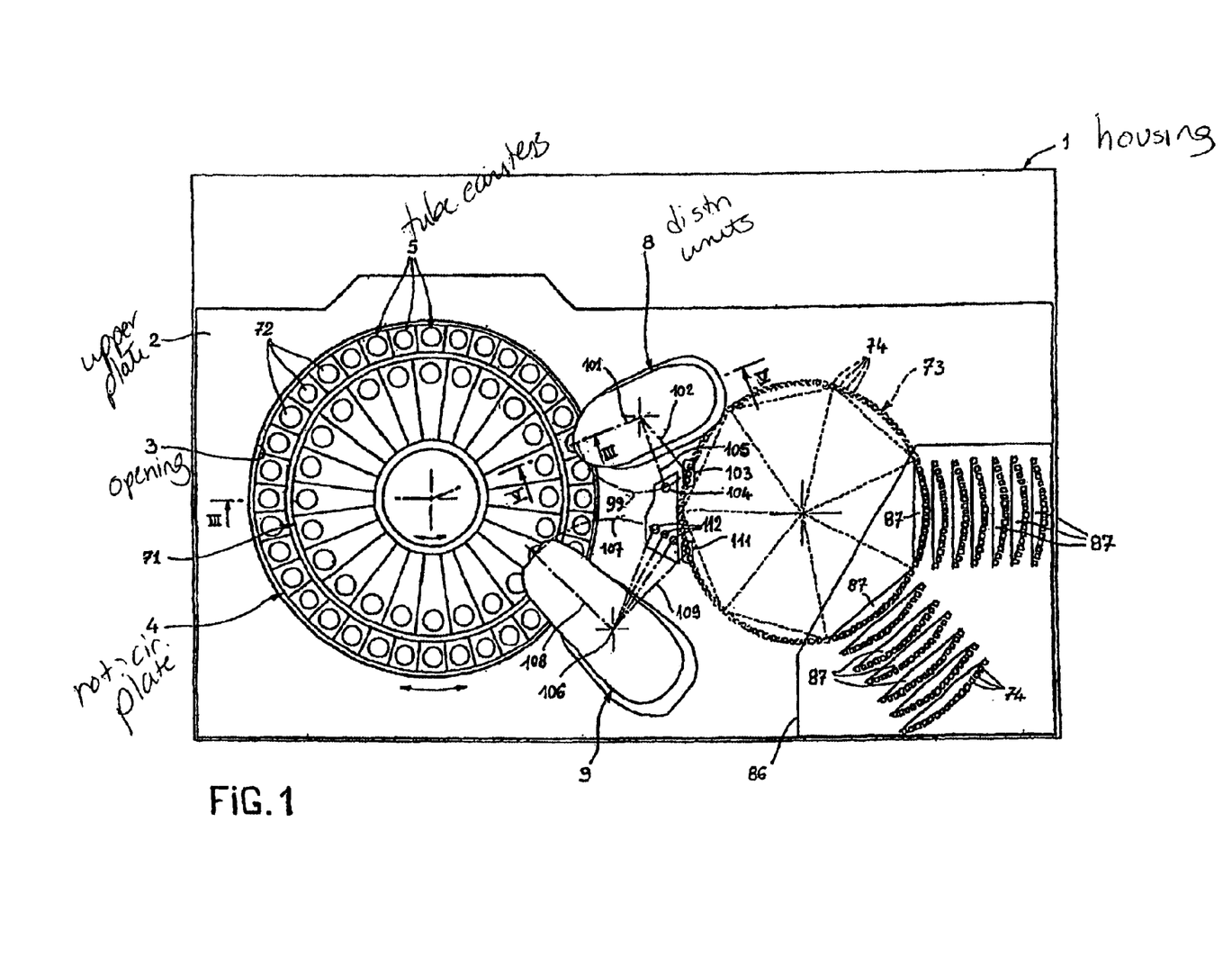
FIG. 1 is a plan view of an analysis robot according to the present invention.

As shown in FIGS. 1 and 3, the reagent carrying plate 71 has a diameter slightly smaller than that of the plate 4 and it is preferably disposed coaxially above this latter plate. The plate 71 is fixed at the upper end of a shaft 75 which is rotatably mounted in bearings 76 and 77, for example roller bearings, installed in a vertical support tube 78 which extends coaxially to within the hollow shaft 13 of the plate 4 and whose lower end is rigidly fixed to the plate 16 of the housing. The shaft 75 passes through a hole in the plate 16 and it can be driven in rotation by means of an electric motor 79, preferably a stepping motor, and by means of a transmission comprising for example two toothed pulleys 81 and 82 fixed respectively to the output shaft of the motor 79 and to the shaft 75, and a toothed belt 83. The motor 79 is mounted on a suitable support (not shown) which is fixed to the plate 16 of the housing. An angular coder 84 associated with the shaft 75 permits knowing at any moment the angular position of the reagent carrying plate 71.

As shown in FIGS. 5 and 6, the plate 73 is located just below the upper plate 2 of the housing and it is preferably disposed in a chamber 85, shown schematically in broken lines, which can be maintained at a desired temperature by suitable thermal conditioning means (not shown). The cover 86 (FIG. 1) hinged on the upper plate 2 of the casing by a hinge, gives access to a temporary storage region in the chamber 85. When the cover 86 is raised, it is also possible to have access to a portion of the periphery of the plate 73. The receptacles 74 are preferably organized by groups each comprising for example 16 receptacles, each group being carried by a rack 87 having, seen from above, the shape of the segment of a circle. As a modification, the receptacle 74 can be constituted by cells formed directly in the racks 87. As shown in FIGS. 5 and 6, each rack 87 is provided with a securement tongue 88 by means of which it can be hooked or fixed in any other suitable manner to the periphery of the plate 73.

The plate 73 can be driven in rotation by an electric motor (not shown), for example a stepping motor, and by a suitable transmission (also not shown). This electric motor and this transmission can be similar to those which were described above with respect to the drive of the reagent carrying plate 71 or with respect to the drive of the plate 4, an angular coder being again provided to give at any moment the angular position of the plate 73.

To as to permit the removal and distribution unit 8 to deliver to the receptacle 74 the samples removed from the sample tubes 6, the two plates 51 and 52 are rotatably mounted, respectively on bearings 89 and 91, for example roller bearings, about a fixed vertical axle 92, whose lower end is fixed to a base plate 93, itself fixed by screws 94 to the upper plate 2 of the chassis as shown in FIG. 5.

The removal and distribution unit 8 can be turned about the axle 92 by means of an electric motor 95, for example a stepping motor, which is vertically aligned above the electric motor 57 and which is fixed to the lower surface of the plate 51. The output shaft of the motor 95 passes through the plate 51 and carries, at its upper end, a toothed pulley 96 in engagement with the toothed belt 97 which passes about another toothed pulley 98 fixed rigidly to the upper end of the axle 92 (FIGS. 2, 5 and 6). As the toothed pulley 98 is fixed, a rotation of the toothed pulley 96 has the effect of turning all of the removal and distribution unit 8 about the axle 92.

An angular coder (not shown) associated with the motor 95, permits knowing at any instant the angular position of the removal and distribution unit 8 relative to the axle 92.

Thus, by activating the motor 95, the needle 45 of the removal and distribution unit 8 can be moved along a path in the arc of a circle 99 (FIGS. 1 and 2) between an angular position 101 in which the needle 45 is located above a sample tube 6 at the periphery of the plate 4, and an angular position 102 in which the needle 45 is located above one of the receptacles 74 at the periphery of the plate 73. In the angular position 102, the needle 45 can be lowered into the receptacle 74 through an opening 103 provided in the upper plate 2 of the housing. A washing well 104, into which the needle 45 can be lowered to be washed and rinsed therein, is provided on the path 99 in an angular position 105 located between the angular positions 101 and 102.

The removal and distribution unit 9, which is designed to take a reagent in a cup 72 selected from cups supported by the reagent carrying plate 71, and to deliver the removed reagent into one of the receptacles 74 carried by the plate 73, can have a structure similar to that described with respect to the removal and distribution unit 8. However, in the removal and distribution unit 9, the foot 63, the rod 64, the spring 66 and the electromagnet 68 are absent, and the needle 45 is replaced by a pipette. The removal and distribution unit 9 can turn as a unit about an axis 106 (FIG. 1) such that the pipette describes a trajectory in the arc of a circle 107 between an angular position 108 in which the pipette is disposed above one of the cups 72 of the reagent carrying plate 71, and another angular position 109 in which the pipette is located above one of the receptacles 74 at the periphery of the plate 73. In the angular position 109, the pipette can be lowered into the receptacle 74 through an opening 111 provide in the upper plate 2 of the housing. The pipette of the removal and distribution unit 9 can also be lowered into any one of the three washing wells 112 located on the path in an arc of a circle 107.

Figure 7:
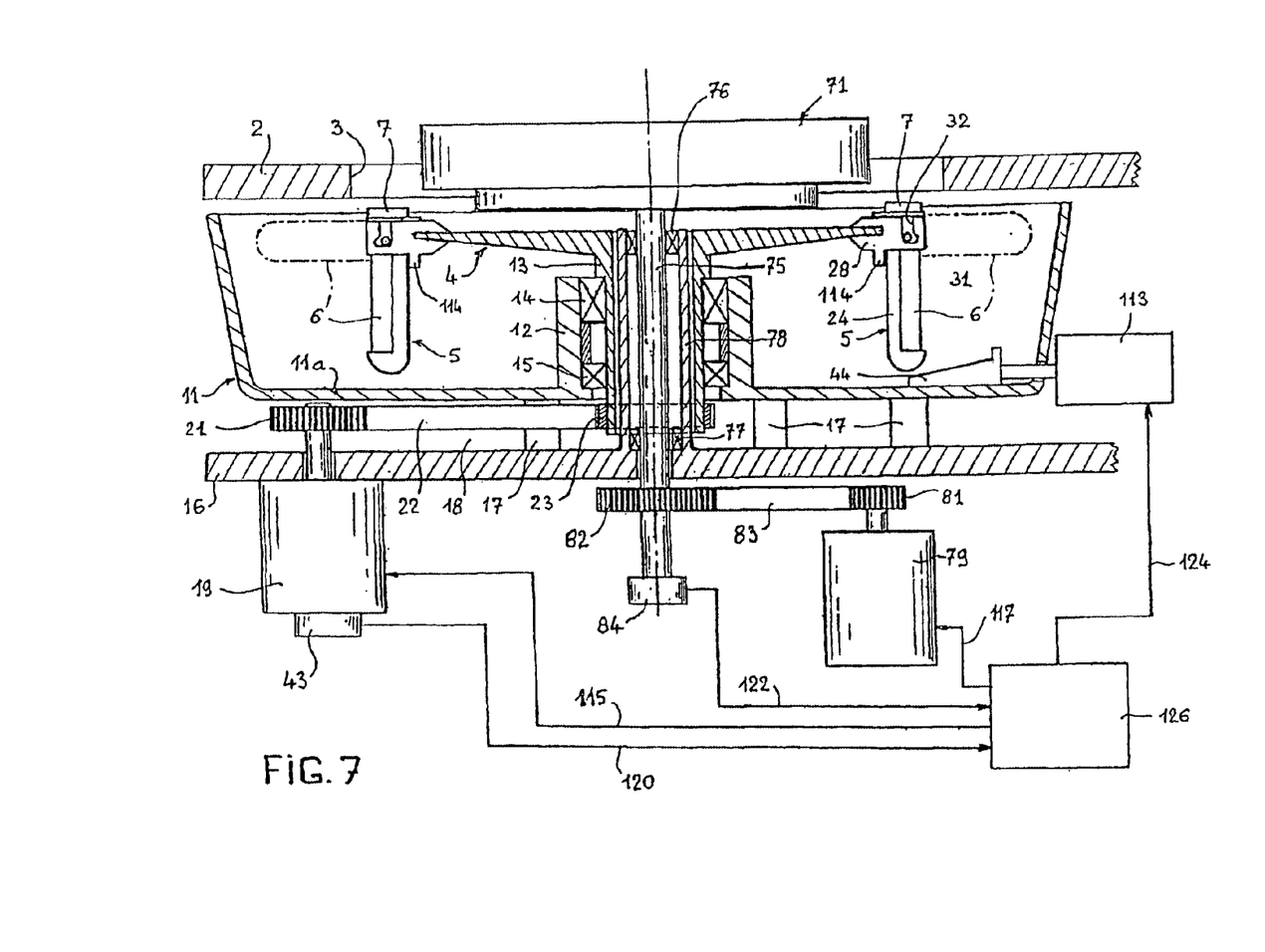
FIG. 7 is a view similar to FIG. 3, showing a modified embodiment.

FIG. 7 shows another embodiment in which the elements which are identical or which play the same role as those shown in FIGS. 3 and 4A, are designated by the same reference numerals, and will not be again described in detail. In the embodiment shown in FIG. 7, the connection 31 with two degrees of freedom comprises no spring 33 and the two pivots 25 of each tube carrying sleeve 24 rest on the bottom of the two notches 32 of the mounting member 28. Preferably, each notch 32 has, in the region of the bottom of the notch, an enlargement directed radially outwardly relative to the axis of rotation of the plate 4.

In FIG. 7, the support means 44 is not constituted by a fixed stop, but by a wedge which can be moved by an actuator 113, for example an electromagnet, between a first position shown in full lines in FIG. 7 and a second position shown in broken lines. In the first position, the wedge 44 does not interfere with the tube carrying sleeves 24 when the plate 4 is rotated.

When a selected sample tube 6 has been brought into correspondence with the removal and distribution unit 8, before the needle 45 of this latter having been lowered, the electromagnet 113 is actuated so as to bring the wedge 44 into its second position, in which it is in contact with the lower end of the tube carrying sleeve 24 and supports the latter in a vertical position such that its two pivots 25 no longer rest on the bottom of the notches 32. Under these conditions, when the needle 45 is lowered and applies to the stopper 7 of the sample tube 6 a vertical force directed downwardly, this force is not transmitted to the circular plate 4, but it is absorbed by the wedge 44.

As shown in FIG. 7, the wedge 44 is preferably constituted by a wedge-shaped piece which can slide, under the control of the electromagnet 113, over a fixed horizontal support and guide surface, for example the bottom 11a of the bowl 11. The direction of movement of the wedge 44 from its first position to its second position is radial relative to the axis of rotation of the plate 4, and perpendicular to the pivotal axis of the tube carrier 5 defined by the two pivots 25. As a result, when the wedge 44 is moved from its first to its second position, it could result that it causes the tube carrier 5 and the sample tube 6 which it contains, to pivot through a certain angle about the axis of the pivots 25 and that, as a result, the sample tube 6 will no longer be vertical at the time the needle 45 of the removal and distribution unit 8 is lowered. To avoid this, each mounting member 28 can be provided with an abutment 114 as shown in FIG. 7.

In the two embodiments, the various active members of the analysis robot, such as for example the electric motors 19, 57, 79 and 95, the syringe 47, the angular coders 43, 62 and 84, the electromagnets 68 and 113, and the code reader 41, are connected respectively by lines 115, 116, 117, 118, 119, 120, 121, 122, 123, 124 and 125 to a control unit 126 (FIGS. 3 and 7) including a computer which manages the operation of the analysis robot. In particular, when the content of the sample tubes 6 must be subjected to centrifugation before being analyzed, the control unit 126 can be programmed to control the electric motor 19 so that it turns at a high speed of rotation during the time necessary to carry out centrifugation, and then that it turns at a slower speed to bring and position successively and selectively the sample tubes 6 into correspondence with the removal and distribution unit 8.

Of course, the electric motors and the angular coders (not shown) associated with the removal and distribution unit 9 and with plate 73 are also connected to the control unit 126. This latter is programmed or programmable to control the rotation of the plates 71 and 73 and the operation of the removal and distribution unit 9 so as to remove, each time this is necessary, at least one reagent from the selected cup 72 of the plate 71 and to deliver the removed reagent into a selected receptacle 74 of the plate 73.

It follows that the embodiments which have been described above have been given purely by way of indicative example and in no way limiting, and that numerous modifications can be supplied by those skilled in the art without thereby departing from the scope of the invention. It is thus that the mounting members could be an integral portion of the plate 4.

What is claimed is:

1. Apparatus for analysis of liquid samples, comprising:
   a support (4) for carrying, in a vertical position, plural sample tubes;
   a removal and distribution unit (8) for removing from each carried sample tube a portion of a contained liquid sample and for distributing a fraction of the removed portion into at least one receptacle (74) as a distributed fraction,
   said removal and distribution unit comprising a hollow needle (45) connected to an aspiration/delivery means (47) and fixed in vertical position to a vertically movable needle carrier (48), and drive means (53, 54, 57, 58, 59, 61) to move the needle carrier,
   said support (4) comprising a circular plate with peripheral tube carriers (5),
   each tube carrier comprising a recess with a vertical access to receive and support a sample tube,
   said circular plate being adapted to turn about a vertical axis to bring in position successively an selectively the tube carriers (5) to a workstation where the removal and distribution unit (8) is located such that the removal and distribution unit can act on a positioned sample tube (6) brought to and positioned in the workstation,
   each tube carrier (5) connected to the circular plate (4) by a connection (31) with two degrees of freedom, a first of the two degrees of freedom being a vertical translatory movement and a second of the two degrees of freedom being a freedom of movement of rotation about a horizontal axis oriented tangentially relative to the circular plate,
   a support means (44) adapted to support the tube carrier (5),
   each tube carrier (5) constituted by a cylindrical sleeve (24) and two pivots (25) defining the horizontal axis with two degrees of freedom,
   an end of each cylindrical sleeve (24) supported by a mounting member (28) secured to the circular plate,
   each of the two pivots (25) resiliently supported in a vertical notch (32) by a flexible spring (33).

2. Apparatus for analysis of liquid samples, comprising:
   a support (4) for carrying plural sample tubes;
   a removal and distribution unit (8) for removing from each carried sample tube a portion of a contained liquid sample,
   said removal and distribution unit comprising a hollow needle (45) connected to an aspiration/delivery means (47),
   said support (4) comprising a circular plate with peripheral tube carriers (5),
   each tube carrier comprising a recess with a vertical access to receive and support a sample tube,
   said circular plate being adapted to turn about a vertical axis to bring in position successively the tube carriers (5) to the removal and distribution unit (8),
   each tube carrier (5) connected to the circular plate (4) by a connection (31) with two degrees of freedom, a first of the two degrees of freedom being a vertical translatory movement and a second of the two degrees of freedom being a freedom of movement of rotation about a horizontal axis oriented tangentially relative to the circular plate,
   a support means (44) adapted to support each tube carrier (5),
   each tube carrier (5) constituted by cylindrical sleeve (24) and two pivots (25) defining the horizontal axis with two degrees of freedom,
   an end of each cylindrical sleeve (24) supported by a mounting member (28) secured to the circular plate,
   each of the two pivots (25) resiliently supported in a vertical notch (32) by a flexible spring (33).

3. Apparatus for analysis of liquid samples in sample tubes (6) closed by a pierceable stopper (7), comprising:
   a support (4) adapted to support, in a vertical position, sample tubes closed by pierceable stoppers (7);
   a removal and distribution unit (8)
   i) to remove, from each sample tube supported by the support, a portion of a liquid sample contained in each sample tube, the removal creating a removed portion of the liquid sample, and
   ii) to distribute at least a fraction of the removed portion of the liquid sample into at least one receptacle (74) for treatment and/or analysis as a distributed fraction,
   said removal and distribution unit comprising
   i) a hollow needle (45) connected to an aspiration/delivery means (47) and fixed in vertical position to a vertically movable needle carrier (48), and
   ii) drive means (53, 54, 57, 58, 59, 61) to move the needle carrier and needle vertically between a first position with a lower end of the needle located at a higher level than a stopper of a positioned sample tube carried by the support, and a second position with the lower end of the needle located within a liquid contained in said positioned sample tube,
   said support (4) constituted by a circular plate with a periphery and provided with several tube carriers (5) disposed at intervals about the periphery,
   each tube carrier comprising a recess with a vertical access to receive and support individual ones of the sample tubes,
   said circular plate being adapted to turn about a vertical axis to bring in position successively and selectively the tube carriers (5) to a workstation where the removal and distribution unit (8) is located such that the removal and distribution unit can act on a positioned sample tube (6) supported by the tube carrier brought to and positioned in the workstation, plural connections (31), each tube carrier (5) connected to the circular plate (4) by a respective one of the connections (31), each of the connections having two degrees of freedom, a first of the two degrees of freedom being a vertical translatory movement and a second of the two degrees of freedom being a freedom of movement of rotation about a horizontal axis oriented tangentially relative to the circular plate, a support means (44), disposed at the workstation, adapted to support from below the tube carrier (5) brought to and positioned in the workstation, each tube carrier (5) constituted by cylindrical sleeve (24) open at an upper end and closed at a lower end and comprising, adjacent the upper end of the corresponding cylindrical sleeve, two aligned pivots (25) defining the horizontal axis of the respective connection (31), the upper end of each cylindrical sleeve (24) being disposed between two legs (26, 27) of a mounting member (28) in the form of a fork, the corresponding fork secured to the circular plate (4) with the corresponding two legs (26, 27) extending radially outwardly of said circular plate, the two pivots (25) of each cylindrical sleeve (24) being supported respectively by the corresponding two legs of the corresponding mounting member (28), each of the two legs (26, 27) of the corresponding mounting member (28) comprising a vertical notch (32) engaging a respective one of the two pivots (25) of the corresponding cylindrical sleeve (24), each of the corresponding two pivots (25) resiliently supported, in a respective one of the vertical notches (32), by a flexible spring (33).

4. Apparatus according to claim 3, characterized in that the cylindrical tube-carrying sleeves (24) are of a transparent material so as to permit reading an individual identification code (39) carried by a label (38) fixed to each sample tube (6) by a code reader (41) installed at a predefined angular position relative to the vertical axis of rotation of the circular plate (4).

5. Apparatus according to claim 3, characterized in that each cylindrical tube-carrying sleeve (24) comprises, in a cylindrical wall, a wide window (42) permitting reading an individual identification code (39) carried by a label (38) fixed to each sample tube (6) by code reader (41) installed at a fixed station in a predetermined angular position relative to the vertical axis of rotation of the circular plate (4).

6. Apparatus according to claim 3, characterized in that each vertical notch (32) is formed in an upper surface of a corresponding leg (26 or 27) and the corresponding flexible spring (33) supports the corresponding pivot (25).

7. Apparatus according to claim 6, characterized in that each mounting member (28) carries a removable retaining means (34), each removable retaining means, in service, retaining each of the corresponding two pivots (25) in the respective vertical notch (32).

8. Apparatus according to claim 3, characterized in that each vertical notch (32) is formed in a lower surface of a corresponding leg (26 or 27) an each flexible spring (33) is constituted by a flexible blade with one end fixed to a lower surface of said corresponding leg and another end that resiliently supports and retains a corresponding pivot (25) in the respective vertical notch.

9. Apparatus according to claim 3, characterized in that, each said cylindrical sleeve is a cylindrical tube-carrying sleeve having a maximum breadth of vertical movement, the support means (44) is constituted by a fixed stop disposed below a lower sleeve end of each cylindrical tube-carrying sleeve (24) brought to and positioned in the workstation, at a vertical distance (d) from said lower sleeve end, said lower sleeve end being smaller than said maximum breadth of vertical movement as permitted by said respective connection (31) and by the corresponding flexible spring (33) when the needle (45) of the removal and distribution unit (8) exerts a vertical penetration force, directed downwardly, on a stopper (7) of an installed sample tube (6) installed in any of said cylindrical tube-carrying sleeves (44).

10. Apparatus according to claim 3, characterized in that each vertical notch (32) is formed in the upper surface of the corresponding leg (26 or 27) of the corresponding mounting member (28) and each pivot (25) rests on the bottom of the corresponding vertical notch.

11. Apparatus according to claim 10, characterized in that the support means (44) is constituted by a wedge, which can be moved by an actuator (113) between a first position in which said wedge does not interfere with the cylindrical tube-carrying sleeves (24) when the circular plate (4) is rotated, and a second position in which said wedge is in contact with the lower end of one cylindrical tube-carrying sleeve brought to and positioned in the workstation and supports said one cylindrical sleeve in a vertical position such that the two pivots (25) of said one cylindrical sleeve no longer rest on the bottom of corresponding vertical notches (32).

12. Apparatus according to claim 11, characterized in that said wedge (44) is constituted by a piece in the form of a wedge which can slide, under control of the actuator (113), over a fixed support and horizontal guidance surface (11a).

13. Apparatus according to claim 12, characterized in that each mounting member (28) comprises an abutment means (114) adapted to prevent the one cylindrical tube-carrying sleeve (24) from pivoting about the horizontal axis and to hold said one cylindrical sleeve in a vertical position when the wedge (44) is moved from the first to the second position by the actuator (113) and comes in the course of this movement into contact with the lower end of said one cylindrical sleeve.

14. Apparatus according to claim 3, characterized in that the circular plate (4) is connected to drive means (19, 21, 22, 23) adapted to turn said circular plate selectively at a first relatively high speed to submit to centrifugation the liquid samples contained in the sample tubes (6) carried by the circular plate, and at a second substantially slower speed than the first speed, to bring and position successively and selectively said sample tubes to and in the workstation.

* * * * *